United States Patent [19]

Bodaness

[11] Patent Number: 5,563,132

[45] Date of Patent: Oct. 8, 1996

[54] TWO-STEP CANCER TREATMENT METHOD

[76] Inventor: Richard S. Bodaness, 5225 Pooks Hill Rd. Apt. 1603-South, Bethesda, Md. 20814

[21] Appl. No.: 263,186

[22] Filed: Jun. 21, 1994

[51] Int. Cl.⁶ .................................................. A61K 31/40
[52] U.S. Cl. ............................... 514/185; 514/2; 514/410
[58] Field of Search ..................................... 514/185, 410, 514/2

[56] References Cited

U.S. PATENT DOCUMENTS

| | | | |
|---|---|---|---|
| 3,027,391 | 3/1962 | Frigerio | 540/131 |
| 4,386,087 | 5/1983 | Lavallee | 540/145 |
| 4,658,023 | 4/1987 | Shudo | 540/145 |
| 4,668,670 | 5/1987 | Rideout | 540/145 |
| 4,935,498 | 6/1990 | Sessler | 540/145 |
| 4,959,356 | 9/1990 | Miura | 540/145 |
| 4,973,718 | 11/1990 | Buchler | 540/145 |
| 4,988,808 | 1/1991 | Morgan | 540/145 |
| 5,109,016 | 4/1992 | Dixon | 540/145 |
| 5,177,073 | 1/1993 | Gulliya et al. | 514/410 X |
| 5,257,970 | 11/1993 | Dougherty | 540/145 X |
| 5,399,583 | 3/1995 | Levy et al. | 514/410 |

OTHER PUBLICATIONS

Panhematin, in Physicians Desk Reference 1995, 49th Edition, 447–448.
Cermak, J., et al., Cancer Research 53: 5308; 1993.
Sagripanti, J. L. and Kraemer, K. H. Jnl. of Biol. Chem. 264: 1729; 1989.
Tkeshelashvili, L. K., et al., Jnl. of Biol. Chem. 266: 6401; 1991.
Aruoma, O. I., et al., Biochem. Journal, 273: 601; 1991.
Stadtman, E. R. and Berlett, B. S., Jnl. of Biol. Chem. 266: 17201; 1991.
Goldstein, S., et al., Free Radical Biology and Medicine, 15: 436; 1993.
Halliwell, B. and Gutteridge, J. M. C., FEBS Letters, 307: 108; 1992.
The Pharmacological Basis of Therapeutics, 8th edition, Edited by Gilman, A. G., et al., pp. 1208–1263 by P. Calabresi & B. A. Chabner, Chapter 52:—Antineoplastic Agents, 1990.
Walling C., Accounts of Chemical Research, 8: 125; 1975.
Russell, G. A., Journal of the American Chemical Society, 79: 3872; 1957.
Gaffney, F. A., et al., American Journal of Cardiology, 52: 607; 1983.
Wang, X., et al., Chinese Medical Journal, 92: 693; 1979.
Oliver, T. H. and Murphy, D. V., The Lancet, 1: 432; 1920.
Mallams, J. T., et al., Progress in Clinical Cancer, 1: 137; 1965.
Chasin, W. D., et al., Archives of Otolaryngology, 85: 47; 1967.
Hien, T. T. and White, N. J., The Lancet, 341: 603; 1993.
Johnson, R. J. R., et al., British Journal of Radiology 41: 749; 1968.
Slaga, T. J., et al., Science, 213: 1023; 1981.

Slaga, T. J., et al., in Radioprotectors and Anticarcinoge edited by Nygaard, O. F., et al., pp. 471–483, 1983.
Arcos, J. C., et al., Chemical Induction of Cancer, vol. 111A, pp. 594–604, 1982.
Figge, F. H. J., et al., Proceedings of the Society for Experimental Biology and Medicine, 68: 640; 1948.
Balla, G., et al., Laboratory Investigation, 64: 648; 1991.
Lin, H., et al., Proceedings of the Society for Experimental Biology and Medicine 187: 7; 1988.
Bonnett, R., Chapter 1, Nomenclature, in The Porphyrins, edited by David Dolphin, vol. 1, Part A, 1978, pp. 1–25.
Smith, K. M., editor, Porphyrins and Metalloporphyrins, 1978, pp. 174–187 in the chapter by J. W. Buchler, and pp. 795–800 in the chapter by J. H. Fuhrhop and K. M. Smith.
Buchler, J. W., Synthesis and Properties of Metalloporphyrins, in The Pprphyrins, edited by David Dolphin, vol. 1, Part A, 1978, pp. 390–474.
Berezin, B. D., Coordination Compounds of Porphyrins and Phthalocyanines, 1981, pp. 13–22.
Inubushi, T. and Yonetani, T., Methods in Enzymology, 76: 88; 1981.
Lavallee, D. K., The Chemistry and Biochemistry of N–Substituted Porphyrins, 1987, p. 175.
Moser, F. H. and Thomas, A. L., The Phthalocyanines, vols. 1 and 2, 1983.
Mew, D., et al., The Journal of Immunology, 130: 1473; 1983.
Mew, D., et al., Cancer Research, 45: 4380; 1985.
Roberts, J. C., et al., Journal of Immunological Methods, 105: 153; 1987.
Brinkley, M., Bioconjugate Chemistry, 3: 2; 1992.
Fawwaz, R., et al. Nuclear Medicine and Biology, 17: 65; 1990.
Kraehenbuhl, J. P., et al., The Journal of Experimental Medicine, 139: 208; 1974.
Zaleska, M., and Wilson, D. F., Journal of Neurochemistry, 58: 107; 1992.
Yamamoto, Y., et al., Analytical Biochemistry, 160: 7; 1987.
Ceresa, R., Polymeric Peroxides, in The Chemistry of Peroxides, edited by S. Patai, 1983, pp. 418–428.
Vasquez–Vivar, J. and Augusto, O., Journal of Biological Chemistry, 267: 6848; 1992.
Sommer, S., et al., FEBS Letters, 172: 267; 1984.
Phillips, J. L. in Chapter 9, vol. 9, Comprehensive Biochemistry, edited by M. Florkin and A. H. Stotz, 1963, p. 55.
Szatrowski, T. P. and Nathan, C. F., Cancer Research, 51: 794; 1991.

(List continued on next page.)

*Primary Examiner*—Richard L. Raymond

[57] ABSTRACT

A two-step cancer treatment method consisting of the initial administration of a cancer-localizing peroxide-reactive metal-ion containing compound, and then administering a peroxide compound to the patient after allowing sufficient time for the localization to the cancer of the metal-ion containing compound to occur. The product of the chemical reaction between the cancer-localizing metal-ion containing compound, and the peroxide compound is an oxidant species which acts to destroy the cancer.

27 Claims, No Drawings

OTHER PUBLICATIONS

Sheppard, C. S. and Mageli, O. L., Peroxides and Peroxy Compounds–Organic, in Kirk–Othmer Encyclopedia of Chemical Technology, third edition, vol. 17, 1982, pp. 27–90.

Hall, R. E., Peroxides and Peroxy Compounds–Inorganic, in Kirk–Othmer Encyclopedia of Chemical Technology, third edition, vol. 17, 1982, pp. 1–26.

Rush, J. D. and Bielski, B. H. J. Journal of Physical Chemistry, 89: 5062; 1985.

Bielski, B. H. J. and Cabelli, D. E., International Journal of Radiation Biology, 59: 291; 1991.

Kanofsky, J. R., Journal of Organic Chemistry, 51: 3386; 1986.

Howard, J. A. and Ingold, K. U. Journal of the American Chemical Society 90: 1056; 1968.

Hawco, F. J., et al., Biochemical and Biophysical Research Communications, 76: 354; 1977.

Koga, S., et al., Archives of Biochemistry and Biophysics, 289: 223; 1991.

Kalyanaraman, B., et al. Journal of Biological Chemistry, 258: 3855; 1983.

Youngman, R. J., et al., Biochemical Pharmacology, 31: 3723; 1982.

The Pharmacolgical Basis of Therapeutics, $8^{th}$ Edition. Edited by Gilman, A. G. et al.; pp. 1202–1208, by P. Calabresi and B. A. Chabner, 1990.

TWO-STEP CANCER TREATMENT METHOD

FIELD OF THE INVENTION

This invention relates generally to methods for the treatment of cancer.

BACKGROUND OF THE INVENTION

The therapy of disseminated cancer is a fundamental problem in clinical medicine. When a cancerous tumor is localized and accessible, it can be surgically removed or treated with radiation therapy. However, once a cancer has metastasized, the prognosis for longterm survival generally decreases markedly, and in addition, there is a marked decline in the general quality of life. When metastasis has occurred, systemic chemotherapy is generally the only therapeutic option available which can be used to prolong life. Although some exceptions exist, the existing drugs used for the systemic chemotherapy of metastasized cancer are palliative rather than curative, and their considerable toxicity results in marked morbidity for the patient.

Heretofore, there have been no known anticancer methods or drugs which involve a two-step method of the type described herein to achieve their active anticancer effect. In contrast, almost all of the known anticancer chemotherapeutic agents are administered in their active form or are metabolically transformed in vivo to their active forms in a nonspecific manner, and therefore all tissues, normal and neoplastic alike, are exposed to the active agent. This accounts for the well known toxicities associated with cancer chemotherapy. Thus, it would be advantageous to have a method of cancer chemotherapy which became active only after localization of the drug to the cancer had occurred, thereby possibly minimizing or reducing the toxic effects on normal tissues. In addition, almost all of the presently available anticancer drugs are considered to act at the level of the genetic apparatus of the cell (The Pharmacological Basis of Therapeutics, eighth ed., 1990. pp 1208–1263). It would therefore also be advantageous to have a method of cancer chemotherapy which acted at the cancer cell membrane instead of within the cell, thereby providing a method by which the internal cancer cell defenses and mechanisms of resistance against anticancer drugs might be bypassed, and thus provide a new or alternative treatment method to assist those patients whose malignancies have proven resistant to conventional anticancer therapies. Heretofore there have been no methods of cancer chemotherapy which achieve these advantages and therefore none lie within the scope of the present invention of a two-step method for the treatment of cancer.

It is known that certain metal ions and metallo-compounds such as copper, iron, and heme, can react with peroxides to generate powerful oxidant species. An example of this is the Fenton reaction in which the ferrous ion reduces $H_2O_2$ to generate the hydroxyl free radical ($OH^\cdot$), a known powerful oxidant, as per the following reaction (Walling, C., Fenton's Reagent Revisited, Accnts of Chemical Research 8:125; 1975):

$$Fe^{2+}+H_2O_2 \rightarrow Fe^{3+}+OH^\cdot+OH^-$$

The hydroxyl free radical is known to be an extremely powerful oxidant species, and is known to react with a wide variety of biological components (such as amino acids, proteins, lipids, carbohydrates, and nucleic acids) with very high reaction rate constants. The hydroxyl free radical can react with hydrogen peroxide to generate the perhydroxyl free radical ($HO_2^\cdot$). The perhydroxyl free radical can dissociate to generate the superoxide free radical ($O_2^{\cdot-}$), dismutate to generate $H_2O_2$ and oxygen, and react with $O_2^{\cdot-}$ to generate $H_2O_2$ and oxygen. $O_2^{\cdot-}$ (but not appreciably $HO_2^\cdot$) can reduce $Fe^{3+}$ to $Fe^{2+}$. These reactions are presented in the following equations:

$$OH^\cdot+H_2O_2 \rightarrow H_2O+HO_2^\cdot$$

$$HO_2^\cdot \rightarrow O_2^{\cdot-}+H$$

$$HO_2^\cdot+HO_2^\cdot \rightarrow H_2O_2+O_2$$

$$HO_2^\cdot+O_2^{\cdot-}+H^+ \rightarrow H_2O_2+O_2$$

$$Fe^{3+}+O_2^{\cdot-} \rightarrow Fe^{2+}+O_2$$

For organic hydroperoxides (ROOH) which react with metal ions, the generation of free radical species from the reaction of the hydroperoxide with peroxide reactive metal-ions can be formulated as per the following two equations, (where Me symbolizes a peroxide reactive metal-ion), which result in the generation of organic oxy ($RO^\cdot$) and peroxy ($ROO^\cdot$) free radicals:

$$ROOH+Me^{n+} \rightarrow RO^\cdot+Me^{(n+1)+}+OH^-$$

$$ROOH+Me^{(n+1)+} \rightarrow ROO^\cdot+Me^{n+}+H^+$$

For organic internal peroxides, the generation of free radical species from the reaction of the peroxide with peroxide reactive metal-ions can be formulated as per the following equation. As used in this specification and in the claims appended hereto, the term organic internal peroxide refers to molecules of the form ROOR', where R and R' are organic moieties which may be identical or different, and wherein both valences of the peroxy (peroxo) —O—O— moiety are bonded directly to carbon. This definition is to be understood to include endoperoxides.

$$ROOR+Me^{n+} \rightarrow RO^\cdot+RO^-+Me^{(n+1)+}$$

It will be recognized by those familiar with the art that free radical reactions are frequently chain reactions, and therefore, once initiated, such reactions can amplify and induce damage far greater in extent than that expected from the number of initiation reactions. It will also be recognized that this amplification factor can sometimes be of major importance.

It will also be recognized by those familiar with the art that the metal-ion mediated free radical generating reactions described above, involve metal-ions which undergo one-electron changes in oxidation state. Metal-ions which undergo two-electron changes in oxidation state (such as tin and lead) can also react with peroxides, but the direct reaction products are generally not free radicals (although it is possible that more distal products may be free radicals). An example of a (non-radical generating) two-electron transfer between a metal-ion and a peroxide is presented in the following equation:

$$ROOH+Me^{n+} \rightarrow RO^-+OH^-+Me^{(n+2)+}$$

Under certain circumstances, singlet molecular oxygen ($^1O_2$) another powerful oxidant, is the reaction product of the reaction between a metal-ion containing compound and a peroxide compound. Spectroscopic evidence for the generation of singlet molecular oxygen (via its 1268 nm emission) has been reported from the reaction of metal-ions with primary, secondary, and tertiary organic peroxides. The mechanism for the generation of singlet oxygen has been most clearly elucidated in the case of secondary peroxides, via the Russell mechanism (J. Amer. Chem. Soc. 79:3872; 1957). Specifically, this consists of the combination of two secondary peroxy free radicals to form an unstable tetroxide, and then the concerted decomposition of the tetroxide to yield an alcohol, a ketone and singlet oxygen ($^1O_2$), as per the following equation (the concerted tetroxide decomposition can result in either singlet oxygen and a ground state ketone, or an excited ketone and ground state oxygen):

$$2R(H)OO^\cdot \rightarrow R(H)OOOOR(H) \rightarrow R(H)OH + RO + {}^1O_2$$

Singlet oxygen is known to be a powerful oxidant of biological components, but is more selective than the hydroxyl free radical. Singlet oxygen has been shown to oxidize certain amino acids, proteins, unsaturated lipids and reduced pyridine nucleotides, and has also been shown to be markedly cytotoxic.

It is to be understood that the specific mediators and mechanisms of the present invention may be extremely complex and may involve, for example, ferryl and perferryl ions as well as other chemical species. Therefore, the discussions presented herein of specific oxidant species and their mechanisms of generation, such as, for example, hydroxyl free radical and singlet oxygen, are understood to be for illustrative purposes only, and thus the present invention is not to be considered limited or constrained in any way to or by the presented mechanisms and species.

There is clinical documentation for the intravenous administration of dilute peroxide solutions to human patients. Hydrogen peroxide has been used intravenously in humans as a contrast agent for clinical echocardiography. Gaffney et al., (American Journal of Cardiology, 52:607; 1983) injected two milliliters of heparinized 0.2 percent hydrogen peroxide intravenously into 36 patients and noted no detectable ill effects. Wang et al., (Chinese Medical Journal, 92:693; 1979) injected 0.5–1 milliliters of 2–3 percent hydrogen peroxide into 100 patients. Eighty-nine were noted to have no untoward reaction whereas eleven did have side effects which were described as rare and slight. The investigators noted that there was no angina, hemiplegia, or mental disturbance, and that they considered the method to be safe and well tolerated. Oliver and Murphy (The Lancet, 1:432;1920 ) used intravenous hydrogen peroxide in the treatment of influenzal pneumonia with beneficial effect. There is also clinical documentation for the intraarterial use of hydrogen peroxide in human patients (Mallams et al., Prog. Clin. Cancer, 1:137; 1965), but caution has been expressed concerning the intraarterial route (Chasin, et al., Arch. Otolaryng. 85:151; 1967). Benzoyl peroxide has been widely used for approximately two decades on thousands of patients for the topical treatment of acne, with no evidence of serious untoward or deleterious effects. Artemisinin and its derivatives are organic endoperoxides used orally for the treatment of malaria in man, and have been reported to be of relatively low clinical toxicity in the doses utilized (Hien and White, The Lancet, 341:603; 1993).

There have been other therapeutic applications of peroxides in man. Hydrogen peroxide as a three percent aqueous solution has been used for many years as an antiseptic for the skin, and has demonstrated no undue propensity for untoward or deleterious effects. It is also available in a gel formulation for the same purpose. In addition, hydrogen peroxide, calcium peroxide, carbamide peroxide, and sodium peroxyborate, have been used in various oral hygiene preparations such as toothpastes and oral rinses. Carbamide peroxide is available in a gel formulation for the treatment of aphthous ulcers. Carbamide peroxide is also approved for instillation into the ear, in order to loosen impacted cerumen.

It is well known by those familiar with the art that the excessive systemic use of hydrogen peroxide can potentially result in the serious even fatal hazard of oxygen embolus, and that this arises from generating concentrations of oxygen above the oxygen solubility limit of the blood. In order to minimize and prevent this occurrance, it has been proposed that hydrogen peroxide be given in concentrations and quantities, and administered at rates, which preclude the blood oxygen solubility limit from being exceeded (Johnson et al., Br. J. Radiol., 41:749; 1968). The importance of the route, dose, and rate of administration bears emphasis. As a separate matter, some organic peroxide compounds, including benzoyl peroxide, have been reported to be carcinogenic in experiments on animals (Slaga, et al., Science, ;713:1023; 1981, Slaga, et al., pp. 471–484, in Radioprotectors and Anticarcinogens, edited by O. F. Nygaard and M. G. Simic, Academic press, 1983, and J. C. Arcos, et al., Chemical Induction of Cancer, vol. ILIA, pp. 595–604, 1982). The clinical significance of this in humans is unknown particularly regarding benzoyl peroxide, since this compound has a long history of clinical use for the treatment of acne without apparent evidence of carcinogenesis. A number of approved anticancer drugs are known to be carcinogenic, but common sense indicates that, if possible and all other things being equal, noncarcinogenic peroxides are to be preferred.

SUMMARY OF THE INVENTION

It is an object of the present invention to provide a two-step method for the in vivo destruction of tissue at a specific locus.

It is another object of the invention to provide a two-step cancer treatment method.

It is another object of the invention to provide a method for the destruction of specific antigens in tissue.

It is yet another object of the invention to provide a treatment for diseases characterized by accumulations of cells such as, for example, polymorphonuclear leukocytes which produce peroxide and/or superoxide. Psoriasis and Reiter's disease are examples of such afflictions.

Yet another object of the invention is to provide a method for the destruction of specific cells which mediate pathologic effects in the host. An example would be the toxic lymphocytes in graft versus host disease.

These and other objects and advantages of the present invention are accomplished by means of a two-step method for generating oxidant species at a specific locus within a patient. Thus, in one preferred aspect, the invention relates to a treatment method, particularly a cancer treatment method, consisting of two steps. The first step involves the administration of a peroxide-reactive metal-ion containing molecule which has the property of localizing to tumor tissue and which also will react with a peroxide to generate oxidant species. Examples would include a metal-porphyrin compound or a metal-porphyrin-antibody compound. The second step occurs after allowing sufficient time for the tumor-localizing compound to localize to the cancer, and involves the administration of a peroxide compound, a peroxide-antibody compound, or of a compound which can generate peroxides or peroxide precursors at the cancer site. The reaction product of the chemical reaction between the peroxide and the tumor-localized metal-ion containing compound is an oxidant species which destroys the cancer.

In one aspect of the invention, the administered peroxide-reactive metal-ion containing tumor localizing compound becomes bound to the cancer cell membrane, particularly when the compound incorporates an antibody or antibody component which localizes to a cancer cell membrane site. Then, when the peroxide compound is subsequently administered to the patient, it reacts with the metal-ion containing compound at the cancer cell membrane instead of at a locus within the cancer cell, and thus the oxidant species arising from the chemical reaction between the peroxide compound and the metal-ion containing compound destroys the cancer cell via the destruction of the cancer cell membrane. This aspect of the invention is relatively unique and has a number of fundamental implications. The first implication is that internal cancer cell defenses against anticancer drugs are bypassed, because the oxidant species does not act within the cell but instead acts at the membrane. A second implication relates to the use of antibodies in cancer chemotherapy. Heretofore, a frequent problem in the use of antibodies to selectively deliver anticancer drugs to the cancer, was that the drug had to somehow gain access to the interior of the cell in order to exert its anticancer effect, because the mechanism of action of the drug involved interference with internal cellular processes. Thus an additional layer of complexity was required in order to achieve a chemotherapeutic effect. In contrast, the present invention does not require entry of the drug into the cancer cell, because the invention can achieve its chemotherapeutic effect at the cancer cell membrane. Third, because the oxidant species exerts its effect at the membrane, the administered peroxide is relatively spared from exposure to the intracellular enzymes glutathione peroxidase and catalase, which metabolically detoxify peroxide. Lastly, it is notable that the mechanism of action of the present invention is different and distinct from the mechanisms of most of the heretofore presently available drugs for cancer chemotherapy, and therefore, the present invention may be of benefit to patients whose cancers have proven resistant to presently available chemotherapeutic modalities.

In another aspect, the present invention is particularly useful for the treatment of disseminated or metastasized cancers as well as for the treatment of localized cancers, for localized cancers which are present in body loci not easily accessible via surgical means, and for the treatment of cancers which have proven resistant to other forms of therapy. It may be applied to both solid tumors and non-solid tumors such as leukemia, to human immunodeficiency virus (HIV) infections and also to disorders such as graft versus host disease. The present invention can also be applied to the ablation of specific antigens in tissue and on cells, and thus ameliorate diseases of antigen immunity. The present invention may be generally adapted to the ablation or destruction of any tissue or tissue component to which the metal-ion containing molecule can be localized after administration. The specific site of localization or binding, depends upon the specific peroxide-reactive metal-ion containing molecule being administered.

PRIOR ART

Metal-porphyrins (Figge, et. al., Proc. Soc. Exp. Biol. Med., 68:640; 1948) and metal-phthalocyanines (N. A. Frigerio, U.S. Pat. No. 3,027,391) are known to have a relative affinity and relatively selective localization to cancerous tissue. There are a number of patents which invoke the use of metal-ions linked to organic compounds in the form of metal-porphyrins, but none of these patents disclose a two-step method for the treatment of cancer and none involve the clinical administration of a peroxide compound. Moreover, in contrast to the present invention, almost all of these metal-porphyrin patents involve either photodynamic therapy wherein photons penetrate into tissue in order to photoactivate a porphyrin, or involve the use of a radioactive metal-ion in order to localize or treat the cancer. The inability of visible light to penetrate deeply into tissue is a major drawback to photodynamic therapy. Entirely separate from photodynamic therapy are the anticancer drugs bleomycin and the anthracyclines. It has been suggested that the mechanism of action of these drugs may involve endogenous in vivo metal-ion chelation and a subsequent reaction with endogenous peroxide. However, in contrast to the present invention, these drugs contain no metal ions, do not involve exogenous peroxide administration, do not involve a two-step treatment method, can be highly toxic, and are considered to act within the cancer cell at the level of the genetic apparatus, rather than at the cell membrane. U.S. Pat. No. 4,386,087 to Lavallee discloses that metallo N-methyl porphyrins have activity against an animal leukemia, and proposes that the mechanism is via methyl release from the porphyrin to serve as an alkylating agent. No peroxide compound is utilized. U.S. Pat. No. 4,668,670 to Rideout et al. discloses the therapeutic use of tin-diiododeuteroporphyrin in mammals to inhibit heme metabolism, to control the rate of tryptophan metabolism, and to increase the rate of heme and iron excretion. No proposal is made for the treatment of cancer, no peroxide compound is utilized, and no oxidant is invoked. U.S. Pat. No. 4,935,498 to Sessler et al. discloses metal complexes of "expanded porphyrins" and their use as photosensitizers in biological systems. No peroxide compound is utilized. U.S. Pat. No. 4,973,718 to Buchler et al. discloses a chemical method for the epoxidation of olefins via rhenium-metalloporphyrins and hydrogen peroxide. This patent is for a synthetic chemical process and does not disclose any applicability to medical treatment. U.S. Pat. No. 4,658,023 to Shudo discloses metal porphyrin derivatives containing a dipyrido[1,2-a:3',2'-d]imidazole moiety, and wherein these compounds are stated to possess enhanced oxygen-dependent DNA cleavage ability and to be effective antitumor agents. No peroxide compound is utilized. U.S. Pat. No. 4,959,356 to Miura et al. discloses boronated porphyrins for boron neutron capture therapy in the treatment of brain tumors. No peroxide compound is utilized and no oxidant is invoked. U.S. Pat. No. 4,998,808 to Morgan and Selman discloses metal complexes of porphyrins, verdins, and benzochlorins for photodynamic therapy. No peroxide compound is utilized. U.S. Pat. No. 5,109,016 to Dixon et al. discloses porphyrins, porphyrin-like compounds, and metal derivatives thereof, for the purpose of inhibiting the human immunodeficiency virus in the absence of light. No anticancer effect is disclosed, no peroxide compound is utilized, and no oxidant is invoked. The reaction products of hemin and hydrogen peroxide have been shown to be cytotoxic to cultured endothelial cells (Lab. Invest. 64:648; 1991) and erythrocytes (Proc. Soc. Exp. Biol. Med. 187:7; 1988) in vitro. No effects on cancer cells is disclosed and there is no disclosure of any treatment for any disease.

DESCRIPTION OF THE INVENTION

In one preferred aspect the present invention comprises a two-step method for the treatment of cancer. The first step utilizes a peroxide-reactive metal-ion containing tumor-localizing compound. One exemplification is a compound which incorporates or consists of a metal-porphyrin or metal-porphyrin-like compound. Examples of such compounds into which metal-ions are to be incorporated are porphyrins, porphyrin derivatives, porphyrin-like compounds, phthalocyanines, phthalocyanine derivatives, and phthalocyanine-like compounds. Further specific examples include hematoporphyrins, etioporphyrins, protoporphyrins, uroporphyrins, mesoporphyrins, coproporphyrins, hematoporphyrin derivative (HPD), porphins, chlorins, phorbins, bacteriochlorins, porphyrinogens, phlorins, purpurins, rhodins, pheophorbides, erythrins, pheophyrins, pheophytins, verdins, corrins, corroles, corphins, sapphyrins and derivatives thereof. Neutral, charged, polar, and nonpolar derivatives are included, as well as compounds chemically linked to or containing one or more of the above. The chemical nomenclature of porphyrins is complex, and such compounds can be named either by a systematic classification as derivatives of porphyrin or via the use of classically used traditional names (R. Bonnett, Chapter 1, in The Porphyrins, Edited by D. Dolphin, vol. 1, pp 1–25, 1978). As described in this specification and in the claims appended hereto, the present invention includes the use of all molecules which can incorporate a metal ion, and which are or can be modified to be tumor-localizing. The invention includes the use of heme, hemin, and hematin. As used in this specification and in the claims appended hereto, the term cancer is meant to be interpreted in the broadest sense, and to include solid and nonsolid malignancies, premalignancies, and tumors which are malignant by virtue of their location such as, for example, within the brain.

The metal ions germane to the present invention include all peroxide-reactive metal ions and metal ions which which become peroxide-reactive when incorporated into a molecule. Examples of metal-ions germane to the invention include the following: copper, iron, nickel, manganese, cobalt, vanadium, chromium, silver, rhodium, ruthenium, technetium, molybdenum, niobium, zirconium, platinum, tin, lead, hafnium, tantalum, tungsten, rhenium, titanium, osmium, mercury, cerium, samarium, europium, and ytterbium. As used in this specification and in the claims appended hereto, the term metal-ion is meant to be inclusive of all metal ions which are peroxide reactive, or which become peroxide reactive when contained in a molecule. In addition, as used in this specification and in the claims appended hereto, the term metal-ion containing, or metal-ion-linked, is meant to be inclusive of conditions wherein one or more metal-ions is included in a molecule via chemical bonding, or wherein one or more metal-ions is included in a molecule via a "cage". This definition includes the coordination bonding of metal ions to porphyrins and phthalocyanines, as for example, in the coordination bonding of iron in heme, hemin, and hematin, and also includes metal-ion chelation.

Examples of metal-ion containing compounds germane to the present invention include metal-porphyrin coordination compounds such as, for example, iron-hematoporphyrin, copper-hematoporphyrin, manganese-hematoporphyrin, heme, hemin, and hematin; and metal-phthalocyanine coordination compounds such as, for example, iron-phthalocyanine, copper-phthalocyanine, and manganese-phthalocyanine. Methods of incorporating metal ions into porphyrins and phthalocyanines are well known to the art. Such methods are discussed in the book entitled Porphyrins and Metalloporphyrins, edited by K. M. Smith, 1975, pages 174–187 and 795–800. Further synthetic methods for metal-porphyrins are discussed in the book entitled The Porphyrins, volume 1, edited by David Dolphin, 1978, chapter 10 (entitled Synthesis and Properties of Metalloporphyrins, by J. W. Buchler). Still further synthetic methods are presented in the book entitled Coordination Compounds of Porphyrins and Phthalocyanines, by B. D. Berezin. Further metal-porphyrin synthetic methods are described in the paper entitled Synthesis of Modified Porphyrins and Metalloporphyrins by T. Inubushi and T. Yonetani, in Methods in Enzymology, volume 76, pp. 88–94, 1981. Yet further metal-porphyrin synthetic methods are discussed in the book entitled The Chemistry and Biochemistry of N-Substituted Porphyrins, by D. K. Lavallee. Further metal-phthalocyanine synthetic methods are presented in the book entitled The Phthalocyanines, by F. H. Moser and A. L. Thomas, 1983. Many metal-porphyrins and metal-phthalocyanines are available from commercial sources. Porphyrin Products, Inc. advises that they are prepared to incorporate most metal ions into most porphyrins, and indicate that they have synthesized, for example, iron-hematoporphyrin IX, copper-protoporphyrin IX, manganese- deuteroporphyrin IX, chromium-mesoporphyrin IX, and cobalt-hematoporphyrin IX. Manganese-phthalocyanine, iron-phthalocyanine, and both tin(II)-phthalocyanine and tin(IV)-phthalocyanine are available from Strem Chemicals, Inc. Cobalt-tetramethoxyphenylporphyrin, cobalt-phthalocyanine, copper-phthalocyanine, and copper-phthalocyanine tetrasulfonic acid tetrasodium salt are available from Eastman Fine Chemicals. As a general example, the structure of a metal-porphyrin is presented as follows, and it is to be understood that Me stands for metal-ion:

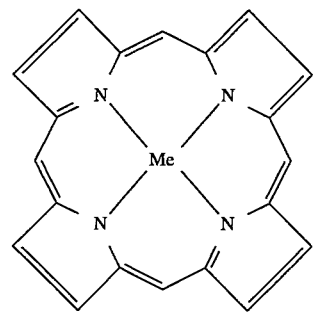

As a specific example, the structure of iron-hematoporphyrin is presented as follows:

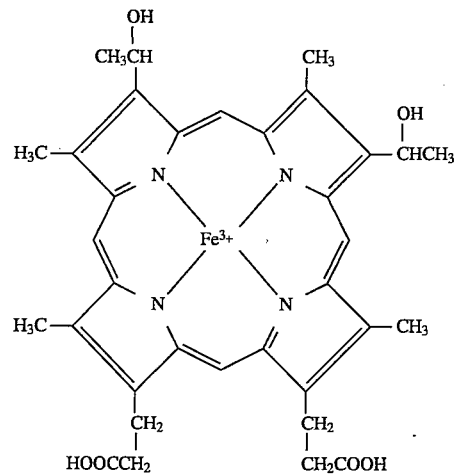

Increased specificity to achieve more exclusive tumor-binding can be achieved by incorporating an antibody or antibody-like compound as part of the peroxide-reactive metal-ion containing compound. As used in this specification and in the claim claims appended hereto, the term antibody is meant to include antibodies (and antibody fragments or components) in the usual immunologic sense, and also any molecule, regardless of size, which achieves site specific or relatively site specific localization in a biological system. While it is known that many metal-porphyrins and metal-phthalocyanines have a selective affinity for cancerous tissue and cancerous tumors, it is also known that this affinity is generally not exclusive, i.e., there is also frequently an affinity for liver and kidney. Therefore, the linking of peroxide reactive metal-ions to anticancer antibodies, and the linking of metal-porphyrins and metal-phthalocyanines to anticancer antibodies facilitates a relatively greater exclusivity of localization to cancerous tissue per se. Methods for the generation of anti-tumor antibodies are well known to those familiar with the art. Similarly, methods for the linking of porphyrins to proteins, and methods for the synthesis of metal-porphyrin-antibody compounds are well known to those familiar with the art. Linking, coupling, spacer, or connecting compounds are frequently employed to connect, link or conjugate relatively small molecules to antibodies or other molecules, and in this specification and in the claims appended hereto, this is to be understood. Mew, et.al., (The Journal of Immunology, 130:1473; 1983, and Cancer Research, 45:4380; 1985) teaches a method for the generation of antitumor monoclonal antibodies, and also teaches a method for the linking of a porphyrin (hematoporphyrin) to the antibody via the use of 1-ethyl-3-(3-dimethyl-aminopropyl)-carbodiimide, whereby the linkage occurs via the carboxyl sidechains of the hematoporphyrin. Roberts, et.al., (Journal of Immunological Methods, 105:153; 1987) set forth a method for the synthesis of a copper-porphyrin-antibody molecule (encompassing copper-67 and N-benzyl-5,1 0, 15,20-tetrakis(4-carboxyphenyl) porphine) via the initial linkage of the porphyrin to the antibody by the use of 1-ethyl-3-(3-dimethylaminopropyl)-carbodiimide HCl and N-hydroxysuccinimide, with the subsequent metallation of the porphyrin-antibody intermediate molecule via the use of $CuCl_2$. Methods also exist for linking small molecules to proteins via groups other than the carboxyl group (Brinker, M., Bioconjugate Chem. 3:2; 1992). Reagents for the linking of relatively small molecules (such as, for example, porphyrins) to antibodies, can be obtained from from Pierce Chemical Company. Fawwaz, et.al., (Nucl. Med. Biol., 17:65; 1990) have taught that porphyrins are preferred for incorporating metal ions into antibodies because: 1) porphyrins have relatively low toxicity, 2) porphyrins have functional groups which allow for chemical conjugation to proteins, 3) porphyrins incorporate metal ions under relatively mild chemical conditions, 4) metalloporphyrins have relatively high retention of metal ions in vivo, and 5) metalloporphyrins when linked to antibodies do not significantly alter the antigen binding site of the antibody.

In addition, there are a number of heme-peptide compounds (from cytochrome c) termed microperoxidases which are included in the present invention, both as separate compounds and when linked to anticancer antibodies via methods well known to those familiar with the art. The microperoxidases containing 8, 9, and 11 amino acids (MP-8, MP-9, and MP-11) derived from horse heart cytochrome c are available from the Sigma Chemical Company via published methods. For MP-8 and MP-9, the human microperoxidase would differ only at amino acid 15 (in the cytochrome c sequence) wherein serine exists in the human and alanine in the horse. Human microperoxidases can be generated by methods known to those familiar with the art. A method has been described for linking MP-8 to an antibody fragment via the use of the N-hydroxysuccinimide ester of p-formyl benzoic acid (Kraehenbuhl, J., J. Exp. Med. 139:204; 1974). As used in this specification and in the claims appended hereto, the term microperoxidase shall be considered to mean a cytochrome c heme-peptide. The structure of horse MP-8 is presented as follows:

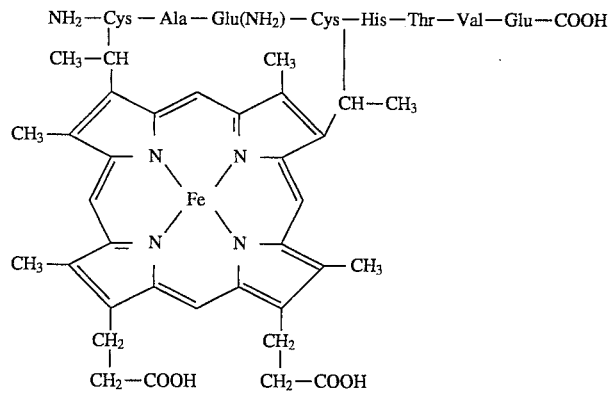

The peroxide compounds contemplated for utilization in the present invention include, for example, hydrogen peroxide; organic peroxides; inorganic peroxides such as sodium peroxyborate tetrahydrate (sodium perborate tetrahydrate) and calcium peroxide; peroxide complexes such as urea hydrogen peroxide, and superoxide salts such as sodium superoxide. In aqueous solution, the superoxide free radical ($O_2^-$) dismutates (via reaction with its conjugate acid, the perhydroxyl free radical) to form hydrogen peroxide, and in biological systems the enzyme superoxide dismutase accelerates dismutation. Examples of organic peroxides include hydroperoxides (ROOH) such as lipid hydroperoxides, and internal peroxides such as artemisinin and its derivatives (an endoperoxide used in the treatment of malaria). Elf Atochem, Inc. is a source of many organic peroxide compounds. Hydrogen peroxide of high purity can be obtained from Solvay Interox and other commercial sources. 1-Hydroperoxycyclohexyl-1-hydroxy cyclohexyl peroxide and tert-Butyl hydroperoxide can be obtained from Pfaltz and Bauer. Artemisinin (T. T. Hien and N. J. White, The Lancet, 341:603; 1993) can be obtained from Aldrich Chemical Company and Sigma Chemical Company. Sodium peroxyborate tetrahydrate can be obtained from Alfa Johnson Matthey and from Fluka Chemika Biochemika. Urea hydrogen peroxide is available from Aldrich Chemical Company. Methods for the preparation of fatty acid hydroperoxides (such as, for example, linolenic acid hydroperoxide, arachidonic acid hydroperoxide, and docosahexaenoic acid hydroperoxide) and of other lipid hydroperoxides (such as, for example, cholesterol hydroperoxide, cholesteryl linoleate hydroperoxide, trilinolein hydroperoxide, phosphatidylcholine hydroperoxide, and phosphatidylethanolamine hydroperoxide) are well known to those familiar with the art (Zaleska and Wilson, Jnl. Neurochem., 58:107; 1992, and Yamamoto, et al., Anal. Blochem., 160:7; 1987). Many other peroxide compounds are available from commercial sources, and include 3-chloroperoxybenzoic acid, 1,1-bis-(tert-butylperoxy)cyclohexane, peracetic acid, monoperoxyphthalic acid, tert-butyl peroxide, 2,5,bis(tert-butylperoxy)-2,5-dimethyl- 3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2, 5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl)dioxy)-cyclohexanol. As used in this specification, and in the claims appended hereto, the term peroxide or peroxide compound is meant to be inclusive of hydrogen peroxide, inorganic peroxides, organic peroxides, peroxide complexes, other compounds containing the peroxy (peroxo) —O—O— moiety, superoxides, and peroxide precursor compounds which generate peroxide species in situ. Examples of organic peroxides include hydroperoxides, internal peroxides, endoperoxides, diacyl peroxides, ketone peroxides, peroxydicarbonates, peroxyesters, dialkyl peroxides, peroxyketals, and peroxyacids. Methods for the synthesis of organic peroxides are well known to those familiar with the art.

After sufficient time is allowed for localization to the tumor of the metal-ion containing, tumor-localizing compound to occur, the peroxide compound is administered to the patient. The duration of the localization time depends upon the specific metal-ion containing tumor-localizing compound being utilized, and can range from being virtually instantaneous to days. Depending on the particular situation, the constituents of the present invention can be administered intravenously, topically, intraarterially, intralesionally, orally, or by intracavitary administration such as, for example, by suppository, by enema (for bowel carcinoma or liver cancer via venous drainage from the bowel), or instillation into the bladder (for bladder carcinoma), or into the peritoneal or chest cavities (to treat either primary cancers or metastatic seeding). The rate of administration, concentration, and amount of peroxide compound administered are a function of the specific peroxide and the route and locus of administration.

At the cancer, a chemical reaction occurs between the peroxide reactive metal-ion containing tumor-localized compound and the administered peroxide. This chemical reaction generates oxidant species, and these oxidant species act to destroy the cancer. This is shown in the following equations:

metal-ion containing compound(MICC) +

$$\text{cancer} \longrightarrow \text{MICC....cancer}$$

-continued
$$\text{peroxide cmpd} + \text{MICC....cancer} \longrightarrow \text{oxidant species to destroy the cancer}$$

indicate localization between the indicated components. This localization can occur via either noncovalent bonding (e.g. binding) or covalent bonding or a combination thereof, depending upon the characteristics of the specific components. Also, as used in this specification and in the claims appended hereto, the terms oxidant, toxic oxidant, and oxidant species (in the context of the reaction between the cancer-localizing metal-ion containing compound and the peroxide compound) are meant to be inclusive of one or more of the products arising either primarily or distally from the chemical reaction between the cancer localizing metal-ion containing compound and the peroxide compound, and which act to destroy the cancer.

There are a number of features of the present invention which are new. The first of these is a two-step cancer treatment method which includes the initial administration to the patient of a tumor-localizing peroxide-reactive metal-ion containing compound such as, for example, a metal-porphyrin, metal-porphyrin-antibody, or a non-porphyrin metal-ion containing moiety linked to an antibody, waiting an appropriate period of time for tumor localization of the metal-ion containing compound to occur, and then subsequently administering to the patient a peroxide compound, so that a reaction occurs between the peroxide and the metal-ion containing compound, resulting in the generation primarily at the tumor site of one or more oxidant species which cause the destruction of the tumor. What is also new is that the present invention may be used to treat metastasized or disseminated cancer, that the invention may be applied to both solid tumors as well as leukemia and other tumors of the blood, and that the oxidant species which destroys the cancer is generated primarily at the cancer site, thus relatively sparing normal tissue.

Another new feature of the present invention is that in one embodiment, the peroxide-reactive metal-ion containing tumor localizing compound becomes localized to the cancer cell membrane, particularly when the compound incorporates an antibody or antibody component which localizes to a cancer cell membrane site. Then, when the peroxide compound is subsequently administered to the patient, it reacts with the metal-ion containing compound at the cancer cell membrane instead of at a locus within the cancer cell. This is represented in the following equations:

metal-ion containing cmpd-antibody(MICCAb) +

$$\text{cancer} \longrightarrow \text{MICC....cancer}$$

$$\text{peroxide cmpd} + \text{MICCAb} \cdots \text{cancer} \longrightarrow \text{oxidant species to destroy the cancer}$$

This is a unique feature of the invention and has a number of fundamental implications. The first implication is that the internal cancer cell defenses against anticancer drugs are bypassed, because the drug does not act within the cell but instead acts at the outside of the cell at the membrane. A second implication relates to the use of antibodies in cancer chemotherapy. Heretofore, a frequent problem in the use of antibodies to selectively deliver anticancer drugs to the cancer, was that the drug had to somehow gain access to the interior of the cell in order to exert its anticancer effect, because the mechanism of action of the drug involved interference with internal cellular processes. Thus an additional layer of complexity was required in order to achieve a chemotherapeutic effect. In contrast, the present invention does not require entry into the cell, because the invention can attain its chemotherapeutic effect at the tumor cell membrane. A third implication is that, by exerting its effect at the membrane, the invention prevents the intracellular peroxide metabolizing enzymes such as catalase and glutathione peroxidase from detoxifying the peroxide, thus increasing the final yield of toxic oxidant. A fourth implication is related to the fact that most of the presently available methods of cancer chemotherapy act within the cell at the level of the genetic apparatus. In contrast, the present invention acts to destroy the cancer cell at the level of the cancer cell membrane, and therefore, because its mechanism of action is different, the invention may be of benefit to patients whose cancers have proven resistant to presently available chemotherapeutic modalities.

Another embodiment of the present invention includes the administration of a peroxide compound consisting of one or more peroxide containing moieties covalently linked to an antibody (or antibody component) which localizes to the cancer cell membrane. Depending upon the specific circumstances, either the same antibody can be utilized as that incorporated in the metal-ion containing compound, or a different cancer-localizing antibody can be utilized which localizes to a different site on the cancer cell membrane. At the cancer, both the metal-ion containing compound and the peroxide compound are localized to the cancer cell membrane due to the antibodies incorporated in each compound. The reaction of the peroxide compound with the metal-ion containing compound results in the generation of toxic oxidant species which act to destroy the cancer. This is set forth in the following equations:

metal-ion containing cmpd-antibody(MICCAb) +

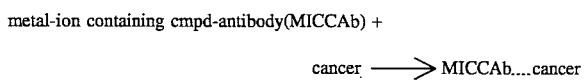

peroxide compound-antibody(PeroxCAb) +

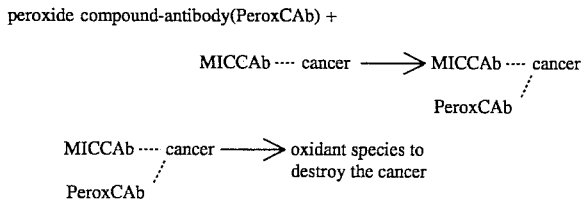

Another version of this embodiment includes the administration of a peroxide compound which incorporates an anti-antibody antibody. This compound consists of one or more peroxide components chemically linked to an antibody (or antibody component) which localizes to the previously administered cancer-localizing metal-ion containing compound-antibody (which localized to the cancer cell membrane). Thus, the peroxide compound incorporates an anti-antibody antibody. In this way, the peroxide compound is targeted to the metal-ion containing compound and thus to the cancer. This is represented in the following equations:

metal-ion containing cmpd-$Ab_1$(MICC$Ab_1$) +

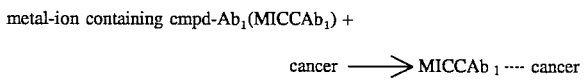

peroxide compound-$Ab_2$(PeroxC$Ab_2$) +

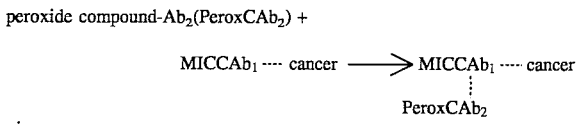

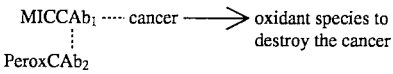

The preceeding two embodiments involving peroxide compounds which incorporate an antibody will be recognized to facilitate the following desirable ends: First, the proximity of the peroxide compound to the metal-ion containing compound will facilitate the chemical reaction between these compounds and thus enhance the generation of toxic oxidant species at the cancer cell membrane. Secondly, the administration of a peroxide compound which incorporates an antibody which localizes to the cancer can decrease or eliminate potential unwanted toxic side effects of the peroxide compound at sites other than the cancer. As a separate matter, it is to be noted that depending on the specific antibody being utilized, more than one peroxide moiety can be linked per antibody. Methods to achieve this are known to those familiar with the art. This plurality of peroxide moieties is desirable, because it increases the extent of generation of toxic oxidant species at the cancer site, thus enhancing the destruction of the cancer. For example, in the case of a polymeric peroxide linked to an antibody, peroxide moieties can be incorporated either by having internal peroxides as part of the polymer chain sequence, or by having hydroperoxides and/or internal peroxides attached to the polymer chain, or by having a combination of both. Polymeric peroxides are well known to those familiar with the art (R. Ceresa, Polymeric Peroxides, pp. 417–428, in S. Patai, The Chemistry of Peroxides, Wiley, 1983). As a further separate matter, it will be appreciated that the presence of peroxide moieties in a molecule which will remain extracellular will enhance the present invention. The reason for this enhancement is that the lack of uptake of peroxide compounds into the cell will inhibit toxicity at noncancer sites due to reaction of peroxide moieties with intracellular heme moieties. An example would be the production of methemoglobinemia due to reaction with hemoglobin in erythrocytes. In contrast, the reaction of the peroxide compound with the metal-ion containing compound which has been targeted to the cancer cell membrane will proceed unimpeded, because this does not require cellular entry.

While the embodiments involving incorporated antibodies have been discussed in relation to the generation of toxic oxidant species at the cancer cell membrane, it will be appreciated by those familiar with the art that these embodiments will also be efficacious if the molecular components of the present invention enter the cancer cell, and the toxic oxidant species arising from the reaction between them are generated intracellularly, and thereby resulting in the destruction of the cancer cell. In addition, it will be appreciated that the present invention is not limited in applicability to cancer alone, but may be applied to the treatment of other diseases as well. Among the diseases contemplated for application of the invention are psoriasis, pustular psoriasis, Reiter's disease, dermatitis herpetiformis, graft versus host disease, leukocytoclastic vasculitis, Sweet's syndrome, human immunodeficiency virus disease (AIDS) and other viral diseases including, for example, those causing hepatitis and those caused by herpes viruses.

Yet another embodiment of the present invention includes (instead of the administration of peroxide compounds per se) the administration of compounds which generate peroxide or superoxide in vivo in order to have continual peroxide generation at the cancer site for reaction with the metal-ion containing tumor-localizing compound. Contemplated examples of such compounds include primaquine, nitrofurantoin, and glycine. The advantage is that this will provide a continual, steady-state concentration of peroxide at the tumor, and thereby facilitates a continual, long-term, steady-state generation of cancer-destroying oxidant. Thus, the cancer cells will be under the bombardment of constant oxidant attack, and will not have an oxidant-free time period in which to recover and regenerate. Hydroxylated primaquine metabolites have been shown to generate superoxide and hydrogen peroxide (Vasquez-Vivar and Augusto, Journal of Biological Chemistry, 267:6848; 1992). In addition, the present invention contemplates the administration of the amino acid glycine, in order to serve as a substrate for the cytoplasmic flavoprotein enzyme d-amino acid oxidase, and wherein the products of this enzymatic reaction are hydrogen peroxide, glyoxylic acid, and ammonia. The hydrogen peroxide can then react with the tumor-localized metal-ion containing compound, resulting in the generation of the cancer destroying toxic oxidant species. Compounds which generate superoxide will also generate peroxide, because in aqueous solutions the superoxide free radical spontaneously dismutates to form hydrogen peroxide, (via the reaction of the superoxide radical with its conjugate acid, the perhydroxyl free radical). In addition, the dismutation reaction occurs at a faster rate via the enzyme superoxide dismutase.

Another embodiment of the present invention is that its chemical constituents can be incorporated into creams, lotions, solutions, ointments, gels, and other dermatologic formulations, which can be utilized for the topical treatment of skin cancer such as, for example, basal cell carcinoma, squamous cell carcinoma, and cutaneous lymphoma (such as mycosis fungoides and Sezary syndrome), for premalignant lesions such as sun-induced actinic keratoses, and for benign lesions of the skin such as psoriasis, seborrheic keratoses, and discoid lupus erythematosus. In this embodiment, it will be recognized by those familiar with the art that selective absorption of the therapeutic constituents (into the pathologic lesions and sparing the surrounding normal skin) will be potentiated by the well known abnormal keratinization present in the pathologic lesions (as compared to the surrounding normal skin), and therefore the generation of oxidant species from the reaction of the metal-ion containing compound and the subsequently administered peroxide, will be localized to the lesions being treated. In addition, there are solvents (such as dimethylsulfoxide) well known to those familiar with the art, which facilitate the absorption of relatively small solute molecules into the skin. Further, the fact that many of these pathologic lesions are distinctly visible facilitates selectivity, because the patient or physician can selectively apply the dermatologic formulation exclusively to the pathologic lesion, and not to the surrounding normal skin. Still further, it is well known to those familiar with the art of dermatologic therapy that occlusion (such as for example, with a plastic film such as commonly available clear polyethylene kitchen wrap) of the treated lesion after topical therapy has been applied, will facilitate the absorption of the topically applied therapeutic constituents into the pathologic lesions. The required duration of occlusion is variable, depending on the particular situation at hand, such as, for example, the thickness of the lesions and the presence of thick scales.

Still another embodiment of the present invention is to administer the tumor localizing compound free of any metal-ions, i.e., without the metal-ion incorporated, and which has the metal ion being subsequently incorporated in vivo. It is known to those familiar with the art that certain metal ions are incorporated into selected organic compounds under extremely mild conditions of reaction such as, for example, the incorporation of $Cu^{++}$, $Co^{++}$, and $Zn^{++}$ into porphyrins (S. Sommer, et.al., FEBS Letters, 172:267;1984, and J. N. Phillips, chapter 2, Physico-Chemical Properties of Porphyrins, page 55, in Volume 9 of Comprehensive Biochemistry, 1963, edited by M. Florkin and E. H. Stotz). It is also known that a number of metal ions are present in human blood and tissues. In this embodiment, the metal-free organic compound such as, for example, a porphyrin, is initially administered to the patient. After sufficient time is allowed for metal-ion incorporation to occur and for tumor localization to occur, a peroxide or peroxide generating compound is administered, and the consequently generated reaction product oxidant species acts to destroy the cancer.

A further embodiment of the present invention is that in certain circumstances endogenously generated peroxide can be utilized to achieve a therapeutic effect, and thereby not require the exogenous administration of a peroxide compound or a peroxide/superoxide generating compound. Under this circumstance where peroxide-generating cells are present in the diseased tissue, the endogenously generated peroxide can react with the peroxide-reactive metal-ion containing compounds which localize to these cells, and thereby generate oxidant species which can destroy these cells. Thus, under these conditions, the peroxide-generating cells provide, in part, the means for their own destruction. It is well known to those familiar with the art that polymorphonuclear leukocytes can generate relatively large quantities of superoxide anion and hydrogen peroxide. It has also been reported that a number of human tumor cell lines generate relatively large amounts of hydrogen peroxide in vitro (Cancer Research, 51:794; 1991 ). It is therefore contemplated that this embodiment may be applied, for example, both to cancer and to diseases involving the polymorphonuclear leukocyte. Among the latter group of diseases which may be ameliorated by this embodiment are psoriasis, pustular psoriasis, Reiter's disease, dermatitis herpetiformis, Sweet's syndrome, leukocytoclastic vasculitis, and all other afflictions which are characterized by cells which generate peroxide. It is noteworthy that present treatments for many of these diseases give poor results, and therefore it would be of benefit to afflicted patients to have a new therapeutic modality such as that described herein. An additional advantage of the invention is that since the peroxide is generated by the very cells which are to be destroyed, toxic effects may be expected to be limited to these involved sites, and thereby spare normal tissue. In this embodiment, the metal-ion containing compound which localizes to the tissue to be destroyed is administered to the patient, and the endogenously generated peroxide reacts with the metal-ion resulting in the generation of oxidant species which destroy the pathologic tissue. In the case of a cancer, the metal-ion containing compound is developed so that it selectively localizes to the cancer. In the case of psoriasis and the other diseases characterized by the presence of polymorphonuclear leukocytes, the metal-ion containing compound is targeted to a component of the pathologic tissue such as, for example, the psoriatic cells or the polymorphonuclear leukocytes present in the psoriatic tissue.

Yet another embodiment of the present invention is that it may be utilized for the treatment of viral diseases such as human immunodeficiency virus disease (AIDS), viral hepatitis, and other viral diseases including, for example, herpes simplex and herpes zoster. In this case, the peroxide-reactive metal-ion containing compound would selectively localize to the offending virus. This is achieved by utilizing an antibody specific to the offending virus, and then chemically linking a peroxide-reactive metal-ion to the antibody as, for example, in the form of a metal-porphyrin. Methods to accomplish this linkage are well known to those familiar with the art, as are methods to generate virus specific antibodies. After administration of the virus-localizing peroxide-reactive metal-ion containing compound, sufficient time is allowed for localization of the compound to the virus to occur. Upon the subsequent administration of the peroxide compound, a chemical reaction will occur between the metal-ion containing compound (localized to the virus) and the peroxide, which will generate an oxidant species which will destroy the virus.

Still another embodiment of the present invention is that it may be adapted to selectively destroy certain undesirable antigens in tissue. Thus, the invention may be applied to address and ameliorate medical problems due to foreign antigens such as transplant rejection in organ transplant surgery and graft versus host disease. In this embodiment, the peroxide-reactive metal-ion containing compound selectively localizes to the undesirable antigen. This can be achieved via utilizing an antibody specific to the antigen to be destroyed, which has been chemically linked to a peroxide-reactive metal-ion as, for example, in the form of a metal-porphyrin. Methods to accomplish this linkage are well known to those familiar with the art, as are methods to generate such antibodies. This antigen-localizing metal-ion containing compound is administered to the patient, and sufficient time is allowed for localization to the offending antigen to occur. Subsequent to the administration and localization of the antigen-localizing metal-ion containing compound, the peroxide compound is administered to the patient so that the oxidant species arising from the chemical reaction between the metal-ion containing compound and the peroxide compound acts to destroy the antigen.

Another embodiment of the present invention is that it may be adapted to selectively destroy certain undesirable cells which are causing or mediating pathological effects in the host. An example would be the toxic lymphocytes in graft versus host disease. In this embodiment the peroxide-reactive metal-ion containing compound selectively localizes to the offending cell. This can be achieved by utilizing a peroxide reactive metal-ion containing compound in which, for example, a metal-porphyrin component is linked to an antibody which localizes to the offending cell. Methods to accomplish such a linkage and to generate such antibodies are well known to those familiar with the art. The metal-ion containing compound (which localizes to the cell to be destroyed) is administered to the patient, and sufficient time is allowed for localization to the offending cell to occur. Subsequently, a peroxide compound is administered to the patient so that the oxidant species arising from the reaction between the metal-ion containing compound and the peroxide compound, acts to destroy the offending cells.

There are features of the present invention that warrant specific emphasis. The first is that the invention potentially offers a new therapeutic modality and thus new hope to patients with metastatic cancer whose disease has proven resistant to conventional chemotherapy. The second feature lies in the ability to selectively localize the point of generation of the oxidant species to the site of the cancer or cancer metastases, thus supporting a relatively limited toxicity toward normal tissue.

It is to be understood that the above specification contains merely certain embodiments of the present invention, and that numerous changes, alterations and variations may be made without departing from the underlying concepts and broader aspects of the invention as set forth in the appended claims. In addition, the above specification should not be construed as limitations on the scope of the invention, but rather as an exemplification thereof. Accordingly, the scope of the invention should not be determined by the presented embodiments, but by the appended claims and their legal equivalents.

I claim:

1. A method for the destruction of tissue comprising in sequence:
   a. administering to a patient a peroxide reactive, metal ion containing compound capable of localizing to tissue to be destroyed,
   b. allowing sufficient time for localization of said compound to said tissue to occur, and
   c. administering to said patient a peroxide compound capable of reacting with said metal ion containing compound to generate a reaction product capable of destroying said tissue, whereby the product of the reaction between said peroxide compound and said tissue localizing metal ion containing compound results in said destruction of said tissue.

2. The method of claim 1 wherein said tissue to be destroyed is a cancer.

3. The method of claim 1 wherein said metal ion is selected from the group consisting of copper, iron, nickel, manganese, cobalt, vanadium, chromium, silver, rhodium, ruthenium, technetium, molybdenum, niobium, zirconium, platinum, tin, lead, hafnium, tantalum, tungsten, rhenium, titanium, osmium, mercury, cerium, samarium, europium, and ytterbium.

4. The method of claim 1 wherein said peroxide is selected from the group consisting of hydrogen peroxide, organic peroxides, inorganic peroxides, peroxide complexes, peroxide salts, and superoxides.

5. The method of claim 1 wherein said metal ion is selected from the group consisting of peroxide reactive metal ions.

6. The method of claim 1 wherein said metal ion containing compound is selected from the group consisting of a metal ion incorporated into porphyrins, porphyrin derivatives, porphyrin like compounds, hematoporphyrins, etioporphyrins, protoporphyrins, uroporphyrins, mesoporphyrins, coproporphyrins, hematoporphyrin derivative, porphins, chlorins, phorbins, bacteriochlorins, porphyrinogens, phlorins, purpurins, rhodins, pheophorbides, erythrins, pheophyrins, pheophytins, phthalocyanines, phthalocyanine like compounds, verdins, corrins, corroles, corphins, sapphyrins, and derivatives thereof.

7. The method of claim 6 wherein said metal ion containing compound includes an antibody which localizes to said tissue to be destroyed.

8. The method of claim 1 wherein said metal ion containing compound includes an antibody which localizes to said tissue to be destroyed.

9. The method of claim 1 wherein said peroxide compound includes an antibody which localizes to said tissue to be destroyed.

10. The method of claim 1 wherein said metal ion containing compound includes an antibody which localizes to said tissue to be destroyed and said peroxide compound includes an antibody which localizes to said tissue to be destroyed.

11. The method of claim 10 wherein said antibody included in said peroxide compound is identical to said antibody included in said metal ion containing compound.

12. The method of claim 10 wherein said antibody included in said peroxide compound is different from said antibody included in said metal ion containing compound.

13. The method of claim 1 wherein said metal ion containing compound includes an antibody which localizes to said tissue to be destroyed, and said peroxide compound includes an antibody which localizes to said antibody included in said metal ion containing compound.

14. The method of claim 1 wherein said metal ion containing compound is selected from the group consisting of heme, hemin, hematin, microperoxidase, and compounds which contain heme, hemin, hematin, or microperoxidase.

15. The method of claim 1 wherein said metal ion containing compound localizes to a membrane of said tissue to be destroyed.

16. The method of claim 1 wherein said peroxide compound is formed in vivo from a peroxide generating compound.

17. The method of claim 1 wherein said tissue localizing metal ion containing compound is administered intravenously, intraarterially, intralesionally, topically, orally, or intracavitarily.

18. The method of claim 1 wherein said peroxide compound is administered intravenously, intraarterially, intralesionally, topically, orally, or intracavitarily.

19. The method of claim 1 wherein said metal ion containing compound and said peroxide compound are administered intravenously, intraarterially, intralesionally, topically, orally, or intracavitarily.

20. The method of claim 1 wherein said peroxide compound is produced endogenously from peroxide generating cells.

21. The method of claim 1 wherein said metal ion containing tissue localizing compound is initially free from metal ions when said compound is administered and wherein metal ions are subsequently incorporated into said compound in vivo.

22. The method of claim 1 wherein said tissue to be destroyed is an antigen.

23. A method for the treatment of cancer with cancer destroying oxidant species, which comprises: administering a peroxide reactive metal ion containing compound which will localize to cancer tissue; waiting a period of time sufficient for said metal ion containing compound to localize to said cancer tissue; and subsequently administering a peroxide compound which is capable of reacting with said metal ion containing compound which is localized to said cancer tissue, to generate said cancer destroying oxidant species.

24. A method for the treatment of disease comprising in sequence:
   a. administering a peroxide reactive, metal ion containing compound, said compound being capable of localizing to a component of said disease,
   b. allowing sufficient time for localization of said compound to said disease component to occur, and
   c. administering a peroxide compound,
whereby the products of the reaction between said peroxide and said disease component localized metal ion containing compound, result in the destruction of said disease component and the treatment of said disease.

25. The method of claim 24 wherein said disease being treated is selected from the group consisting of cancer, precancer, noncancer, benign lesion, actinic keratosis, basal cell carcinoma, squamous cell carcinoma, seborrheic keratoses, psoriasis, pustular psoriasis, Reiter's disease, dermatitis herpetiformis, graft versus host disease, leukocytoclastic vasculitis, Sweet's syndrome, and diseases caused by viruses.

26. The method of claim 24 wherein said peroxide compound is produced endogenously from peroxide generating cells.

27. The method of claim 24 wherein said peroxide compound is formed in vivo from a peroxide generating compound.

* * * * *